Figure 1:
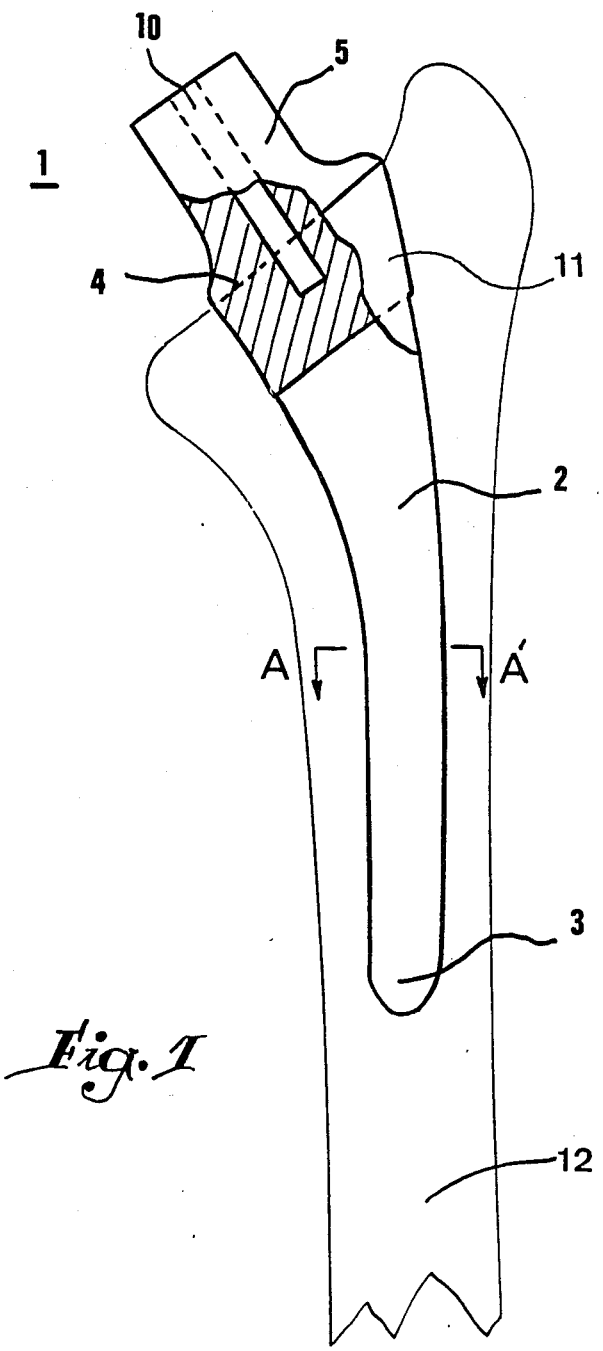

United States Patent [19]

Maï et al.

[11] Patent Number: 4,756,711
[45] Date of Patent: Jul. 12, 1988

[54] SELF-LOCKING PROSTHESIS, AND METHODS FOR PRODUCING AND FOR FITTING IN SAME

[76] Inventors: Christian Maï, 74 boulevard des Belges, 69006 Lyons; Yves Crassas, Clinique Saint Charles, 38150 Roussillon, both of France

[21] Appl. No.: 945,670

[22] Filed: Dec. 23, 1986

[30] Foreign Application Priority Data

Dec. 24, 1985 [FR] France ................. 85 19365

[51] Int. Cl.$^4$ ............................ A61F 2/28; A61F 2/30
[52] U.S. Cl. ................................. 623/23; 623/16
[58] Field of Search ..................... 623/16-23; 128/92 YM

[56] References Cited

U.S. PATENT DOCUMENTS 4,170,990 10/1979 Baumgart et al. ............. 128/924 N
4,520,511 6/1985 Gianezio et al. ............. 128/92 YM

FOREIGN PATENT DOCUMENTS 2483218 12/1981 France ............................ 623/23

Primary Examiner—Richard J. Apley
Assistant Examiner—David Isabella
Attorney, Agent, or Firm—Wall and Roehrig

[57] ABSTRACT

A self-locking prosthesis of which the pin, for insertion into a bone, produced in a biologically compatible material, is split through its width and through part of its length, so as to form at least two separate branches, characterized in that the material constituting the pin has a sharp memory effect and a martensite transformation temperature Ms lower than the human body temperature.

4 Claims, 3 Drawing Sheets

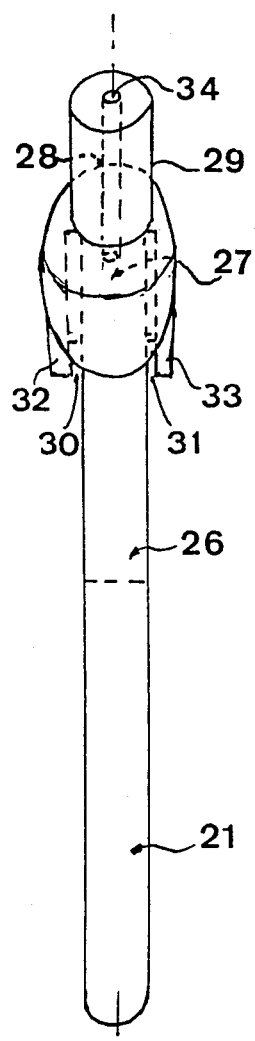
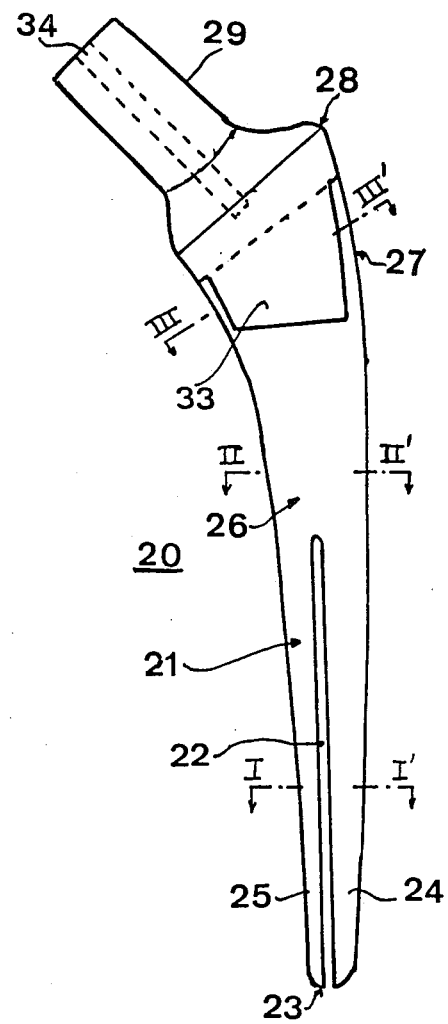
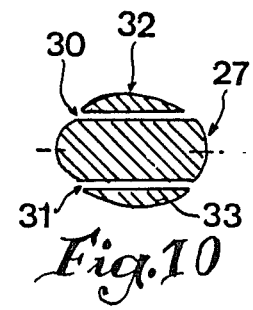
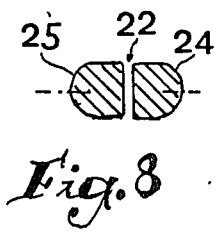
Fig. 7
Fig. 6
Fig. 10
Fig. 9
Fig. 8

SELF-LOCKING PROSTHESIS, AND METHODS FOR PRODUCING AND FOR FITTING IN SAME

The invention relates to a self-locking medical prosthesis; it also relates to a method for producing said prosthesis.

Conventionally, a prosthesis essentially comprises a pin designed to be inserted in a bone, either with a view to strengthening the bone or with a view to acting as a support for a replacement articulation.

The following description and claims refer more particularly to a hip prosthesis, but this is solely by way of example and non-restrictively, as the invention finds other applications, such as for example in other types of articulations or, as already indicated, to reinforce any type of bone.

A conventional hip prosthesis is essentially composed of three separate parts which are, respectively:

a femoral pin, designed to be inserted in the thigh bone or femur;

a cupule, designed to be engaged in the cotyloid cavity of the hip to be reinforced;

a prosthetic neck, topped by a sphere, joining the pin to the cupule, designed to form the actual articulation.

Heretofore, a number of pins of different nature, different longitudinal shapes or different cross-section, have already been proposed. The problem is to find a way of securing the pin inside the bone (femur).

It has for example been proposed to form a threading on the tapered pin, and to engage said pin into a hole made in the bone, in the manner of a screw. Although this technique is widely spread, it has the disadvantage of weakening the bone and creating, after a time, a certain amount of play.

It has also been proposed to secure the pin inside the bone by way of a cement, for example a cement based on acrylic polymer, such as methylpolymethacrylate. But this cement does not wear well, with time and with the stresses due to body movements and weight. The effect is a reduction of the mechanical properties of the cement, hence a certain risk of the prosthesis loosening. Also, during the cement polymerization reaction, the temperature of the cement easily goes up to 70° C., which is relatively high and can cause necroses of the bone tissue. Finally, if for various reasons, it becomes necessary to change the prosthesis, the operation becomes problematic if not impossible.

In Patents FR-A-2 483 218 and EP-A-0050533, it has been proposed to provide a longitudinal slit in the pin in order to give a certain resiliency to the point and thus help the insertion of the pin into the bone which normally always requires force in order to lock the pin in position in the medullary canal. However, this solution, like all the others known to this day, with the exception of the solution whereby the pin is provided with a threading, makes it difficult, if not impossible to subsequently remove the pin, so that the prosthesis cannot be fitted in children or adolescents.

It is the object of the present invention to overcome these drawbacks by proposing a new type of self-locking prosthesis in which the pin is readily produced and inserted, without the need of cements or other locking means such as screw-threads, so that all the properties of the bone in which the pin is to be inserted are preserved.

The self-locking prosthesis according to the invention, of which the pin, for insertion into a bone, is produced in a biologically compatible material and is slit through its width and over part of its length, so as to form at least two separate branches, is characterized in that the material constituting the pin has a sharp memory effect and a martensite transformation temperature $M_s$ lower than the human body temperature.

$M_s$ is the common and usual scientific symbol for "Martensite start", i.e. the start temperature of martensite transformation of a material.

Accordingly, the invention consists in producing the pin of the prosthesis in a material which has a sharp memory effect, and a martensite transformation temperature lower than the human body temperature, then in providing in said pin separate longitudinal branches, so that by simply rising the temperature to nearly the human body temperature, the branches which constitute the pin take on a slightly spread out shape compared with their initial position, shape of which they have acquired the sharp memory effect by a known process.

Advantageously, in practice:

the pin should be cylindrical, oval, tapered towards its point, smooth or screwed, and comprises, two separate branches, which are also tapered and which, depending on the case, are either closed in (temperature lower than the martensite transformation temperature $M_s$), or spread out (temperature higher than $M_s$)

the part of pin facing that carrying the branches, such as for example the prosthetic neck, is provided with a bore designed to receive either a heating member, when the points of the branches are meant to be spread out, or a cooling member, when on the contrary, said points are meant to be closed in the martensite transformation temperature ($M_s$) of the material constituting the pin is advantageously between 0° and 37° C., and preferably between 10° and 20° C.

According to a preferred embodiment of the invention, the pin of the prosthesis essentially comprises three distinct portions, which are, starting from the point.

a first end portion, extending over about half the length of the pin, and which is provided with a longitudinal slit, a second, middle portion which is solid, a third portion situated close to the junction of the pin with the head, namely at the level of the trochanter, which is provided with two parallel slits, orthogonal to the slit of the first portion, and which extend over a considerable part of the height of said third portion.

In practice, said parallel slits are cut in the mass of the third portion.

This particular disposition enables an excellent distribution of the tightening all along the medullary canal of the bone, hence improving the engagement, without making the pin fragile with a slit which would spread from the point to the head.

The sharp memory effect phenomenon is due to the reversible thermo-elastic martensite transformation. This phenomenon is wellknown, therefore it will not be explained in detail here. It consists in conferring to a material a shape which is treated with a temperature $T_1$ higher than the martensite transformation temperature $M_s$, then in conferring to it another shape at a temperature $T_2$ lower than $M_s$, and finally in repeating this operation several times as a function of the nature of the alloy used, in order to confer to this material its final memory sharp. The invention consists in applying that very wellknown phenomenon to the specific field of medical prostheses.

The materials used must of course be biologically compatible with the medium to which they are intended. Also, as already indicated, these materials must have a sharp memory effect and a martensite transformation temperature Ms which is less than the human body temperature. Temperature Ms is dependent on the concentration of the alloy constituents and is found to be accessible in the literature. Suitable materials to this effect are alloys based on titanium-nickel, copper-manganese, copper-zinc, platinum-iron, copper-aluminum-zinc. According to an advantageous embodiment, the prosthesis can be coated with a protecting layer, in particular of a layer of biocompatible material, such as gold or titanium, deposited by any conventional means, and even a layer of ceramics, subject of course to such protecting layer being biologically compatible with the one medium to which it is intended.

The selection of the material to constitute the pin is essentially governed by factors such as cost price, mechanical strength, biological inertia and machining conditions.

As already indicated, the pin comprises in its lower part two or more branches, which can be produced by any conventional method, such as molding, forging or fritting. It has been found that beyond four branches, the cost of the prosthesis is unnecessarily increased without any proportional improvement, but on the contrary, with a risk of embrittlement in the case of small prosthesis.

The invention also relates to a method for producing the pin for such a self-locking prosthesis. Said method consists:

first of all, in producing a prosthesis pin in a material having a sharp memory effect and a martensite transformation temperature Ms which is less than the human body temperature;

in providing in said pin, through its width and through part of its length at least two separate branches;

then, in heating the pin to a temperature T1 which is higher than Ms while spreading out the ends of the branches of the pin;

in cooling the spread-out pin down to a temperature less than Ms while closing in the ends of the spread-out branches;

and finally, in repeating, several times, these last two operations T1 (spreading out) and T2 (closing-in) until the branches of the pin have acquired a sharp memory of two shapes, one spread-out (T1) and one closed-in (T2).

The invention will be more readily understood on reading the following description of examples of embodiment with reference to the accompanying drawings in which:

FIG. 1 diagrammatically illustrates a longitudinal section of the femoral pin of a hip prosthesis according to the invention.

Figure 2:
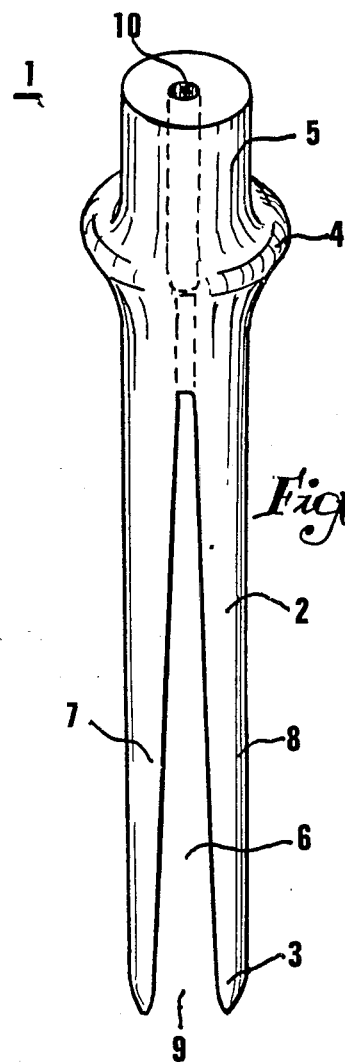
Figure 3:
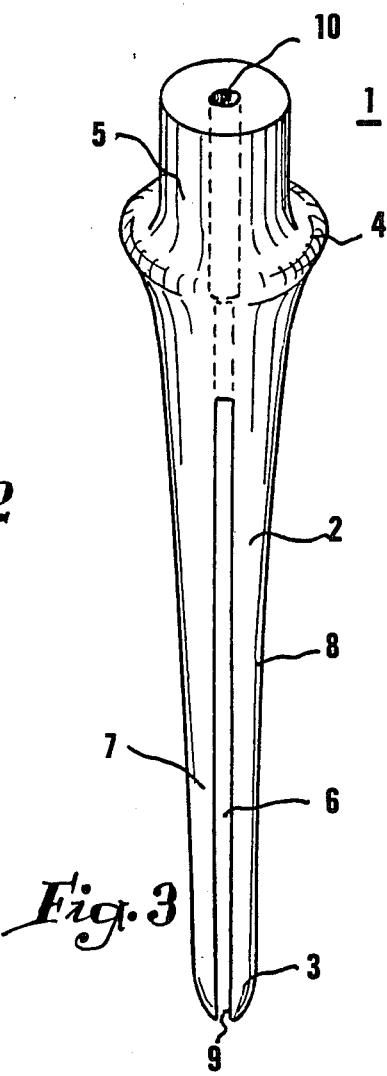

FIGS. 2 and 3 illustrate a front view of said femoral pin seen, respectively, in a position with the branches spread-out (FIG. 2), and in a position with the branches closed-in (FIG. 3).

Figure 5:
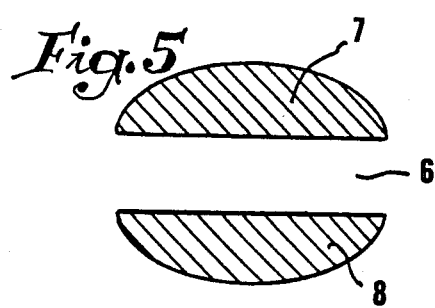
Figure 4:
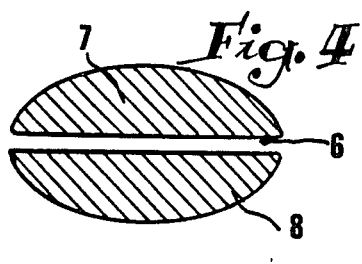

FIGS. 4 and 5 illustrate a cross-section along axis AA' of FIG. 1, respectively in the branches spread-out position (FIGS. 2 and 5) and in the branches closed-in position (FIGS. 3 and 4), but on a larger scale for better comprehension.

FIGS. 6 to 10 diagrammatically illustrate a preferred embodiment of the invention, in, respectively, longitudinal view (FIG. 6), front view (FIG. 7) and cross-section along line I—I' (FIG. 8), along line II—II' (FIG. 9) and along line III—III' (FIG. 10).

The femoral pin designated in general by reference (1) essentially comprises a pin proper (2) which is tapered downwardly into a point (3) and provided at its opposite end, with a supporting flange (4) and a prosthetic neck (5) designed to receive the articulation sphere.

A slit (6) of about 1.5 mm is machine-cut into the pin (2) over approximately half the length of the pin (2). Said slit is cut in the bending direction of the pin (1), but it can also be cut in another direction. The slit thus defines two separate branches (7) and (8).

The material which constitutes the pin (1) is a titanium-nickel alloy (Atomic percentage: 49.3% titanium and 50.7% nickel) of which the martensite transformation temperature Ms is close to 15° C.

Mechanically, at room temperature, a wedge is introduced in the space (9) defined at the end (3), so as to spread out the two branches (7) and (8) in such a way as to have, at said end (3), a gap of about 6 mm (FIG. 5). This operation being carried out at a temperature T1 higher than Ms (15° C.), the pin acquires a first sharp memory effect of that spread-out shape.

The wedge is removed from the point (9), and the pin is dipped into iced water while the end (3) of the spread-out branches (7) and (8) are closed in, for example with a strong clamp. The pin thus acquires another sharp memory effect of the closed-in shape, since the temperature T2 of 0° is lower than Ms.

Operations T1 and T2 are repeated ten times in succession.

The resulting femoral pin (1) has a sharp memory effect of the spread-out shape (T1) and of the closed-in shape (T2), but its shape at room temperature is that with the elementary branches spread out (FIG. 5). Advantageously, the peripheral section of the point in spread-out position (FIG. 5) is substantially similar to the peripheral section of the unsplit part of the pin (FIG. 2) in order to ensure fitting and locking in position in the hole provided to this effect in the thigh bone (12).

The femoral pin (1) also comprises a bore (10) provided in the prosthetic neck (5) and penetrating in rather notable manner into the solid part of the head (11) of the pin (1). Advantageously, said part (11) comprises in known manner cavities or microporosities designed to help the subsequent proliferation of the bone tissues during the new growth. Likewise, these microrugosities can cover the entire pin (1).

When a surgeon has to fit a prosthetic pin according to the invention, he prepares, in known manner, a hole in the thigh bone (12). Then, to close in the spread-out ends of the branches (7) and (8), he dips the pin in iced water. The ends of the branches are thus brought in, one towards the other, by the plastic memory effect. The surgeon can then insert the pin easily in the hole prepared to this effect, without having to use any cement. He then introduces into the bore (10) a heating element such as a battery-supplied resistor. When the temperature of the whole pin (1) rises above 15° C., the branches (7) and (8), under the plastic memory effect, spread out progressively until they are pressed with force against the sides of the hole provided in the medullary canal of the bone (12), moving apart, as illustrated in FIG. 5.

In this way, the pin is firmly locked in position.

If, for any reason, the surgeon wants to remove the prosthesis, even in the middle of the surgical operation, he only needs to introduce a cooling element into the bore (10). As soon as the temperature of the pin (1) goes down below 15° C., the branches (7,8) close in, under the effect of said cooling member. It becomes then possible to pull the pin out without any effort, and to put it back in or if necessary to change it.

According to another embodiment of the invention, there is no need to introduce the heating element into the bore (10) as the temperature is raised progressively by exchange with the human body.

Thus, as long as the temperature of the pin remains above the temperature Ms, the prosthesis remains firmly and homogeneously locked in position. To loosen said prosthesis at any time and for any reason, it is enough to cool the pin down to a temperature below Ms and this by any means. Loosening thus occurs smoothly and without risk of osseous traumatism.

Contrary to the prior art, the pin is fitted smoothly and the fitting operation may be repeated several times during the surgical operation or even long after. Consequently, this type of prosthesis can even be used with children or adolescents since it is always possible to remove the pin as a function of the child's growth.

According to the preferred embodiment shown in FIGS. 6 to 10, the pin (20) of said prosthesis has a first portion (21) which comprises a single longitudinal slit (22) extending from the point (23) and over approximately half the length of the pin (20) in order to form two separate branches (24,25) (FIG. 6,8).

Said slit portion (21) is then connected to a second solid portion (26) shown in FIG. 9.

Said portion (26) is in turn connected with a third portion (27) situated close to the junction (28) of the pin (20) with the head (29), namely at the level of the trochanter. According to one characteristic of the invenition, said third portion (27) comprises two parallel slits (30-31) cut orthogonally to the slit (22) (FIGS. 6-10) and extending (FIG. 7) through nearly the entire height of said third portion (27).

Thus, the slits (30,31) form two parallel faces (32,33) placed on either side of (27) but monobloc therewith. Reference (34) designates a bore similar to (10).

The assembly (21, 26, 27, 32, 33) is therefore monobloc, in a martensite material.

The sharp memory effect is conferred to said assembly as in the previous case.

This disposition ensures an excellent stability by ensuring a firm application of the branches (24,25) against the medullar canal and the faces (32,33) at the level of the trochanter, which prevents the rotation of the pin (20).

The prostheses according to the invention are particularly adapted for the hips or other articulations.

What is claimed is:

1. A self-locking prosthesis comprising a pin for insertion into a bone, said pin including a point at one end and a head at the opposite end, said pin being formed of a biologically compatible material having a sharp memory effect and a martensite transformation temperature (Ms) that is lower than the human body temperature, said pin including:
   a first end portion having a longitudinal slit extending from the said point along approximately half the axial length of the pin to divide the first portion of the pin into two separate branches;
   a second solid middle portion; and
   a third portion, close to the junction of the pin with the head having slits formed therein that are substantially orthogonal to the longitudinal slit of the first portion and which extend over part of the axial length of said third portion.

2. The self-locking prosthesis of claim 1 wherein the said head is provided with a bore designed to receive a heating element or a cooling element.

3. The self-locking prosthesis of claim 1 wherein the pin is in a one piece material and wherein the third portion comprises two parallel slits cut in the mass of the said third portion and extending through nearly the entire axial length of said third portion.

4. The self-locking prosthesis of claim 1 wherein the material of the pin is in a titanium alloy having a martensite transformation temperature (Ms) between 10° to 25° C.

* * * * *

UNITED STATES PATENT AND TRADEMARK OFFICE
CERTIFICATE OF CORRECTION

PATENT NO. : 4,756,711
DATED : July 12, 1988
INVENTOR(S) : CHRISTIAN MAI

It is certified that error appears in the above—identified patent and that said Letters Patent is hereby corrected as shown below:

Col. 2, lines 4, 11, 19, 56 and 66 please change "sharp" to --shape--.

Col. 3, lines 4, 34, and 48 please change "sharp" to --shape--.

Col. 4, lines 24, 29 and 34 please change "sharp" to --shape--.

Col. 6, line 19 please change "sharp" to --shape--.

Signed and Sealed this

Twenty-fifth Day of June, 1991

Attest:

HARRY F. MANBECK, JR.

*Attesting Officer*  *Commissioner of Patents and Trademarks*